United States Patent
Kawasaki et al.

(10) Patent No.: US 8,019,399 B2
(45) Date of Patent: Sep. 13, 2011

(54) OPTICAL MEASUREMENT APPARATUS FOR LIVING BODY

(75) Inventors: Shingo Kawasaki, Matsudo (JP);
Noriyoshi Ichikawa, Moriya (JP);
Naoki Tanaka, Saitama (JP)

(73) Assignee: Hitachi Medical Corporation, Tokyo (JP)

( * ) Notice: Subject to any disclaimer, the term of this patent is extended or adjusted under 35 U.S.C. 154(b) by 1395 days.

(21) Appl. No.: 10/578,725

(22) PCT Filed: Nov. 1, 2004

(86) PCT No.: PCT/JP2004/016226
§ 371 (c)(1),
(2), (4) Date: May 10, 2006

(87) PCT Pub. No.: WO2005/046483
PCT Pub. Date: May 26, 2005

(65) Prior Publication Data
US 2007/0142719 A1    Jun. 21, 2007

(30) Foreign Application Priority Data
Nov. 12, 2003   (JP) .................................. 2003-381910

(51) Int. Cl.
*A61B 5/1455*   (2006.01)

(52) U.S. Cl. ......................................... 600/310; 600/323

(58) Field of Classification Search .................. 600/322, 600/336, 310, 323, 473, 476
See application file for complete search history.

(56) References Cited

U.S. PATENT DOCUMENTS

| 4,596,254 A | 6/1986 | Adrian |
| 6,264,591 B1 * | 7/2001 | Keen et al. ...................... 493/4 |
| 6,701,170 B2 * | 3/2004 | Stetson ......................... 600/323 |
| 7,025,728 B2 * | 4/2006 | Ito et al. ......................... 600/500 |
| 7,463,916 B2 * | 12/2008 | Kawasaki et al. ............. 600/310 |
| 2002/0085741 A1 | 7/2002 | Shimizu |
| 2003/0088164 A1 | 5/2003 | Stetson |
| 2003/0120164 A1 | 6/2003 | Nielsen |
| 2004/0171919 A1 * | 9/2004 | Maki et al. .................... 600/310 |

FOREIGN PATENT DOCUMENTS

| JP | 2000-163569 | 6/2000 |
| JP | 2001-000407 | 1/2001 |
| JP | 2001-251646 | 9/2001 |
| JP | 2002-150265 | 5/2002 |
| JP | 2002-177281 | 6/2002 |
| JP | 2004-299814 | 10/2004 |
| JP | 2005-035535 | 2/2005 |

* cited by examiner

*Primary Examiner* — Eric Winakur
*Assistant Examiner* — Marjan Fardanesh
(74) *Attorney, Agent, or Firm* — Antonelli, Terry, Stout & Kraus, LLP.

(57) ABSTRACT

A principal component analysis or an independent component analysis is conducted on the living body signals, e.g., local cerebral blood amount change signals obtained by the living body optical measurement to extract and display multiple component signals thereof. Signals other than the component signals containing noise are selected from these component signals automatically or manually, and the local cerebral blood amount change signals are reconstructed by using selected signals. The reconstructed signals is displayed and further subjected to the component analysis or the reconstruction as appropriate, and used for the profiling of information necessary for the diagnosis. Consequently, high-precision target signals can be obtained by completely removing external noise included in the living body signals, particularly the noise which cannot be adequately removed by the moving average and the filtering processings.

16 Claims, 7 Drawing Sheets

OPTICAL MEASUREMENT APPARATUS FOR LIVING BODY

FIELD OF THE INVENTION

The present invention relates to an apparatus which measures information inside a scattering object, especially a living body, by using light (herein after referred to as "optical measurement apparatus"). Particularly, it relates to a technology to obtain necessary local cerebral blood amount change signals precisely by removing noise signals included in the blood amount change signals.

BACKGROUND OF THE INVENTION

The optical measurement apparatus can measure blood circulation, blood flow and changes of the hemoglobin amount inside the living body by irradiating visible to infrared light onto the part of an object to be examined and by measuring a light that reflects inside the living body. When the optical measurement is performed while the object is loaded with stimulation or task, changes in blood circulation, blood flow and changes in the hemoglobin amount are observed, as compared with that without such stimulation or load. Accordingly, by comparing these changes with the known change patterns, distinctive attributes and characteristics of the subject can be identified.

Since this optical measurement apparatus can obtain information of the living body non-invasively and easily without restraining the subject, the clinical applications of the optical measurement apparatus is being put into clinical use.

The clinical applications of the optical measurement apparatus include the identification of an epileptic focus, the identification of the linguistic area in the pre-examination of epileptic surgery and the diagnosis of cerebral disease. In the examination to identify the linguistic area, for example, the area is identified by measuring local cerebral blood amount change signals for the right and left temporal lobes attributable to the language stimulation load and comparing the range of thus obtained local cerebral blood amount change signals. This is a very important examination to reduce the damage of cerebral function accompanying the removal of an epileptic focus, and a technique for accurately identifying the area is demanded.

However, the superimposition of the local cerebral blood amount change signals by the signals inside the living body and various outside noise signals including apparatus noise and . . . signals attributable to body movement makes it difficult to obtain highly precise local cerebral blood amount change signals.

Figure 3:
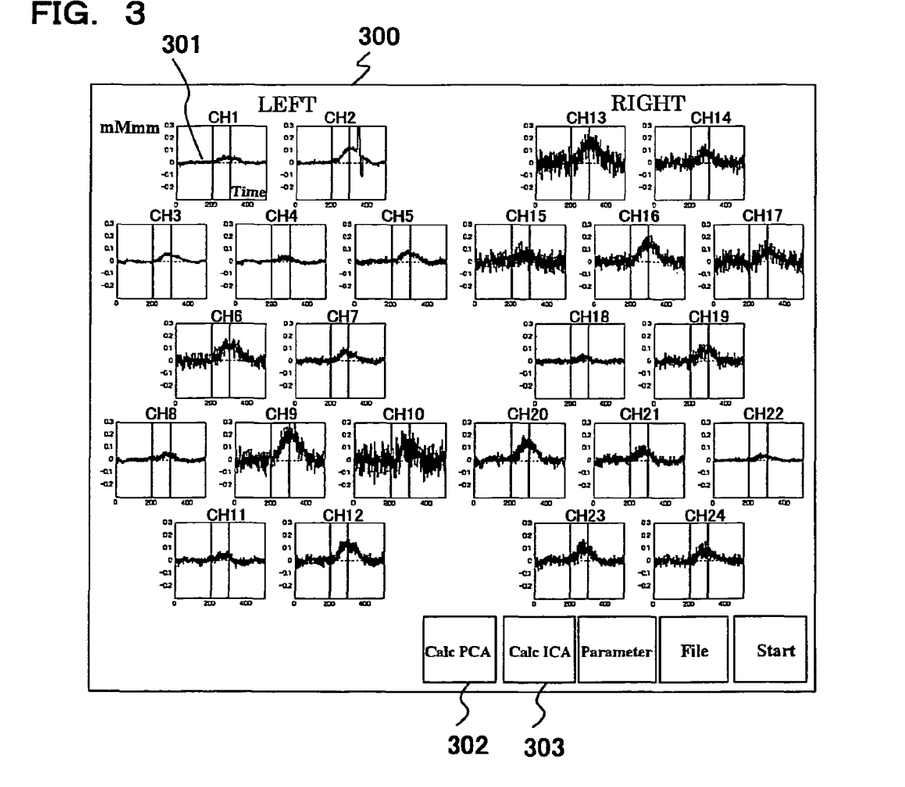
FIG. 3 is a diagram showing a hemoglobin amount change signal in each channel, obtained by the measurement shown in FIG. 2.

The moving average and the filtering, as described in Patent Document 1, have been used to remove these noises, but they often failed to remove the noise sufficiently. For example, the spike noise components which generate at CH2 of the graph in FIG. 3 are characterized by a broad frequency band. In order to remove such noises by filtering or moving average, the filter should be applicable to a broader band or the moving average should be applicable for a longer period of time. However, they have such disadvantage that necessary local cerebral blood amount change signals are also removed.
Patent document 1: Japanese Patent Application No. 2002-177281

DISCLOSURE OF THE INVENTION

Problems to be Solved by the Invention

Accordingly, the objective of this invention therefore is to provide an optic measurement apparatus for living body, which can remove noise, regardless of the characteristics of the noise, without distorting the amount of information on the signals to be targeted and obtain highly precise target signals.

Means for Solving the Problems

In order to achieve the afore-mentioned objective, an optical measurement apparatus for living body of the present invention comprises a means for irradiating visible to infrared light onto an object to be examined, a means for detecting the light transmitted inside the living body of the object and generating signals corresponding to the amount of detected light, a signal processing means for processing said signals and generating biological signals of the object and a means for displaying the biological signals generated by the afore-mentioned signal processing means, and is characterized in that the signal processing means comprises a means for separating the biological signals into multiple component signals and a signal reconstruction means for reconstructing biological signals by using specified component signals in the multiple component signals, excluding the component signals which contain noise.

An optical measurement apparatus for living body of the present invention comprises a means for irradiating a visible to infrared light onto the multiple positions of an object to be examined, a means for detecting a light irradiated from the afore-mentioned multiple positions and transmitted inside the living body of the object and generating measurement signals measured at the multiple positions which are determined by the numbers of irradiation and detection sites, a signal processing means for processing measured signals from the afore-mentioned detection means and generating waveforms showing changes in substances inside the object at the afore-mentioned multiple measurement positions and a display means for displaying results of processing (such as the afore-mentioned waveforms) by the afore-mentioned signal processing means, wherein the signal processing means comprises a signal separation means for separating the afore-mentioned waveforms into multiple component waveforms and a signal reconstruction means for reconstructing waveforms showing changes in the substances inside the object by using specified component waveforms among the afore-mentioned multiple component waveforms.

The separated component signals and the reconstructed signals are displayed on the display means, respectively.

In the optical measurement apparatus for living body of the present invention, preferably, a signal processing means comprises at least two different signal separating means. For example, at least one of them analyzes major components of biological signals and separates them into multiple component signals. Or it performs independent component analysis of biological signals and separates them into multiple component signals.

In the optical measurement apparatus for living body of this invention, preferably, the signal processing means comprises a signal selecting means for selecting specified component signals to be used by the signal reconstructing means. The signal selecting means, for example, selects specified component signals based on correlation values between component signals and a pre-determined reference signal. Alternatively, specified component signals are selected based on the standard deviations of differential waveforms of component signals. Or, specified component signals are selected based on both of them.

In the optical measurement apparatus for living body of this invention, preferably, the signal processing means comprises a user interface means which enables users to select specified component signals to be used by the signal reconstructing means. For example, on the display means a multiple principal component waveforms or independent component waveforms and a selection box for selecting these principal component waveforms or independent component waveforms are displayed.

On the display means, for example, a correlation value box for inputting the correlation value and/or a standard deviation box for inputting the afore-mentioned standard deviations are displayed.

A method of removing noise of this invention is a method of removing noise from biological signals which are obtained by irradiating a light onto the positions to be examined of the object and detecting a light transmitted through the examination positions, and comprises a step for conducting component analysis of aforementioned living body measurement signals and separating them into multiple component signals and a step for reconstructing living body measurement signals by using appropriate component signals of aforementioned multiple separated component signals.

The step for separating the signals into multiple component signals comprises a step for performing the principal component analysis of multiple component signals and a step for performing the independent component analysis of multiple component signals. Either or both of these steps may be performed.

In this invention, the noise removing method may comprise a step for separating the living body measurement signals reconstructed in the reconstructing step into multiple component signals and a step for reconstructing them. In this invention, preferably, the noise removing method further comprises a step for selecting certain component signals from the multiple separated component signals. This step selects certain component signals, by using, for example, correlation values between component signals and a pre-determined reference signal and/or standard deviations of the differential waveforms of the component signals.

EXPLANATION OF SYMBOLS

10 . . . light source unit, 20 . . . optical measurement unit, 31 . . . signal processing unit, 32 . . . control unit, 32 . . . storage unit, 20 . . . input/output unit, 40 . . . probe.

PREFERRED EMBODIMENT OF THE INVENTION

Embodiments of the optical measurement apparatus for living body (hereinafter referred to as "optical measurement apparatus") of this invention are explained below with reference to the attached drawings.

In the explanation below the amount of hemoglobin (including oxygenated, de-oxygenated and total hemoglobin) is measured as a parameter in the optical measurement for living body. However, the optical measurement apparatus of this invention measures not only hemoglobin but it can also measure other substances in the living body which absorbs near infrared light, such as cytochrome.

Figure 1:
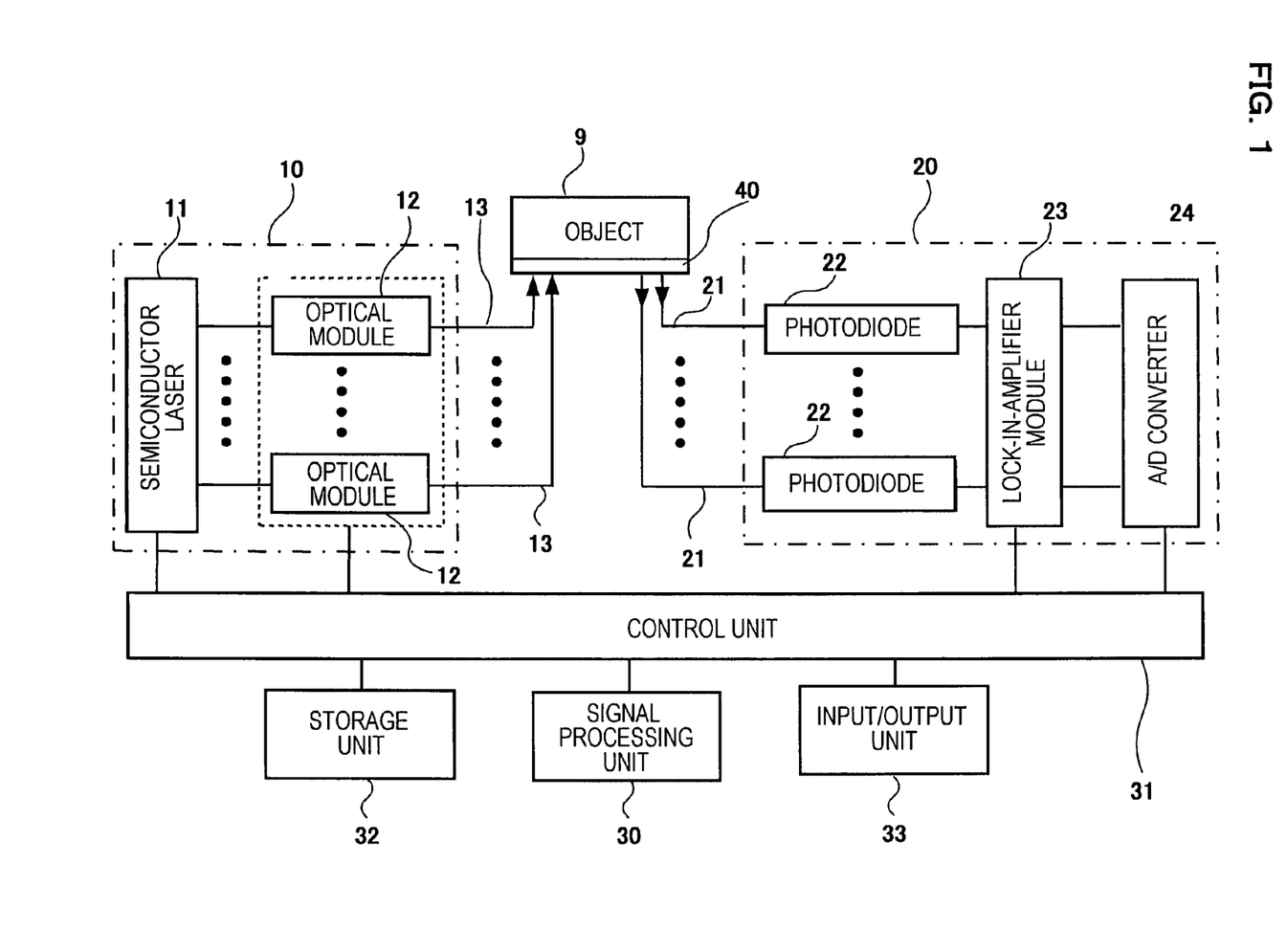
FIG. 1 is a block diagram outlining the optical measurement apparatus for living body of this invention.

FIG. 1 is a block diagram illustrating a configuration of the optical measurement apparatus of this invention. This optical measurement apparatus is equipped mainly with a light source unit 10, which irradiates near infrared light onto a living body, an optical measurement unit 20, which measures a light transmitted through the living body (including a light transmitted and reflected inside the living body. Hereinafter referred to as "transmitted light") and converts them into electric signals and a signal processing unit 30, which calculates the local cerebral blood amount change signals, concretely the changes in the hemoglobin level in blood, as a living body information based on the signals from the optical measurement unit 20 and displays the results of calculation. Further, this optical measurement apparatus is equipped with a fitting member 40, which makes the tips of the optical fibers 13 for guiding the light from the light source unit 10 contact the measurement position of an object to be examined 9 and the tip of the optical fiber 21 for guiding a transmitted light from the object 9 to the optical measurement unit 20 contact the measurement position of the object 9. This fitting member 40 is called, along with the tips of the optical fiber, as a measurement probe.

The light source unit 10 comprises a semiconductor laser 11, which emits the light of multiple wavelengths in the range from visible to infrared, for example 780 nm and 830 nm, a multiple optical modules 12 equipped with a modulator for modulating the light of these two wavelengths at multiple different frequencies and an optical fiber for irradiating a light. The lights of two different wavelengths emitted from the semiconductor laser 11 are mixed, modulated to different frequencies at each optical module, transmitted through the optical fiber 13 and irradiated onto the examination positions of the object.

The optical measurement unit 20 comprises a photo-electric transducer such as photodiode 22, which is connected with the optical fiber 21 and converts a light guided by the optical fiber 21 to electric signals corresponding to the amount of light, a lock-in-amplifier module 23, which input electric signals from the photodiode 22 and selectively detects modulated signals corresponding to the irradiating positions and wavelengths and an A/D converter 24, which performs A/D conversion of the signals from the lock in amplifier module 23. The lock-in-amplifier module 23 comprises at least the same number of lock-in-amplifiers with that of signals to be measured.

A probe 40 comprises sockets for connected with optical fiber, which are configured on a matrix to ensure that the tips of optical fiber for irradiation and the tips of optical fiber for detection are arranged alternately, wherein the size of the matrix, including 3×3 and 4×4, differs according to the examination positions. The light detected by the optical fiber for detection is the mixture of the lights irradiated from, for example, four optical fibers for irradiation adjacent to said optical fiber for detection, and by selecting different modulated signals by these optical fibers for irradiation at the lock-in-amplifier 23, the information on the point (measurement point) between the tip of optical fiber for detection and the tip of adjacent optical fiber for irradiation can be obtained. These measurement points correspond to the channels detected by the lock-in-amplifier 23, and the 3×3 matrix probe, for example, provides 12 measurement points between the irradiation and detection points, and can perform optical measurement of 12 channels.

The signal processing unit 30 is connected with the optical measurement unit 20 through the control unit 31, which controls the whole apparatus, processes voltage signals (digital signals) sent from the optical measurement unit 20 and converts them to the signals indicating the living body information, concretely, the local cerebral blood amount change signals indicating the hemoglobin concentration at the measurement positions or produces a topographic image. This signal processing unit 30 is accompanied by a storage unit 32, which stores digital signals sent from the optical measurement unit 20 and the processed data and an input/output unit 33, which is equipped with a displaying means (monitor) to display the results of processing at the signal processing unit 30 and a means to input commands necessary for the measurement and the signal processing at the control unit 31.

The signal processing unit 30 is equipped with, in addition to the afore-mentioned functions to produce images, the functions to extract signals, which show the features of the task loaded to the subject at the measurement, from the hemoglobin change signals measured at each measurement channel and to identify, based on the task-related signals, the measurement positions (channels) which are most reactive to the task.

In the optical measurement apparatus of this configuration, the optical measurement is conducted by irradiating a light modulated at different frequencies by the optical fiber for irradiation 13 from the probe 40, converting the lights transmitted inside the body and guided by the optical fiber for detection 21 into electrical signals by each photodiode, detecting them at every measurement point located between irradiation and detection positions by lock-in-amplifier 23 and obtaining the hemoglobin-amount-change signals converted into the blood level of hemoglobin at the measurement position. The hemoglobin-amount-change signals measured at each measurement point undergo various kinds of analyzing at the signal processing unit 30, and the results of the profiling are displayed on the monitor of the input/output unit 33.

Figure 2:
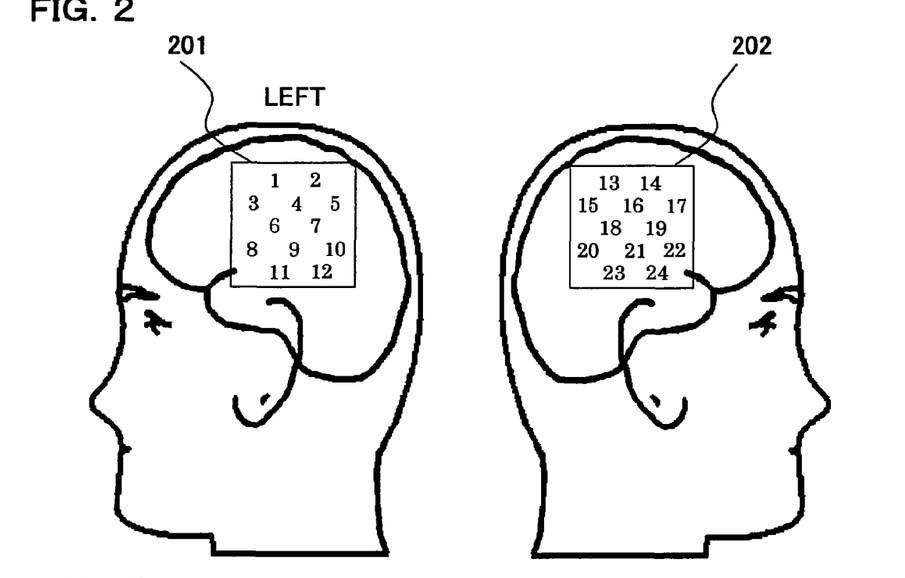
FIG. 2 is a block diagram showing the relationship between measurement site and measurement point (channel).

FIG. 2 shows the measurement of the right and left temporal lobes of the object to be examined. For the example shown in the figure, the measurement data were obtained on total 24 channels, comprising 12 channels each on the left (Ch1-Ch12) and the right (Ch13-Ch24) temporal lobe. The measurement was performed by loading a specified task, difference from the data measured without loading task is obtained as hemoglobin-amount-change-signals. The hemoglobin amount change signals obtained for each channel are shown, for example, by channel as Graph 301 as shown in FIG. 3. In Graph 301, vertical and horizontal axes show the time and mMmm (millimole/millimeter unit: the number of moles encountered during measurement of millimeter unit), respectively, while the length of task loading is expressed by two vertical lines, which show the start and the end of the loading. Terms before and after the loading are stabilizing terms in which no stimulation is imparted.

The hemoglobin-amount-change-signals thus measured contain not only the signals as original living body reactions but also various superimposed noises. The signal processing unit 30 separates noise from these hemoglobin change signals and reconstruct (restore) the hemoglobin change signals by using noise-removed components.

Figure 4:
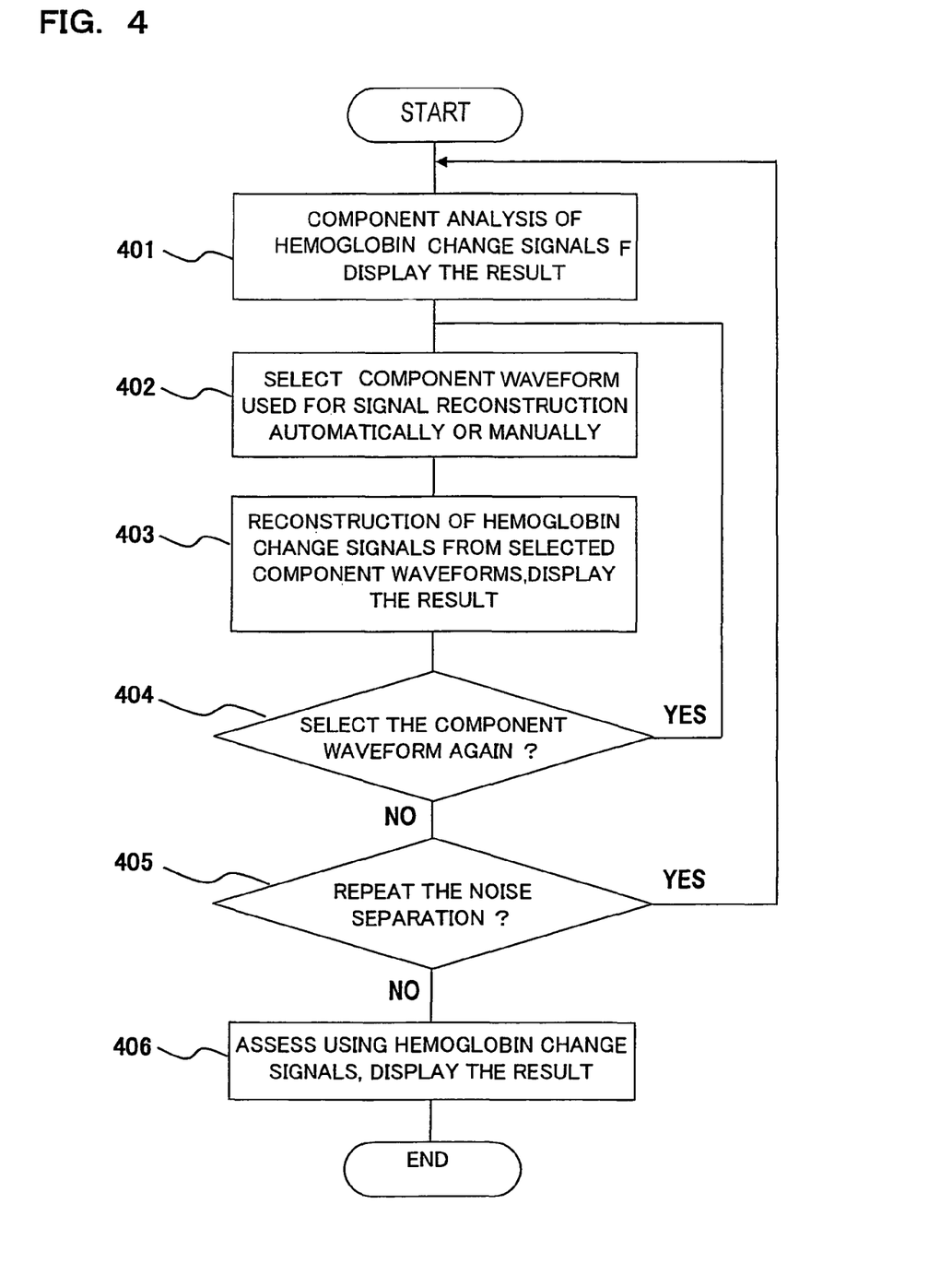
FIG. 4 is a flowchart showing the procedures for processing signals in the optical measurement apparatus for living body of this invention.
Figure 5:
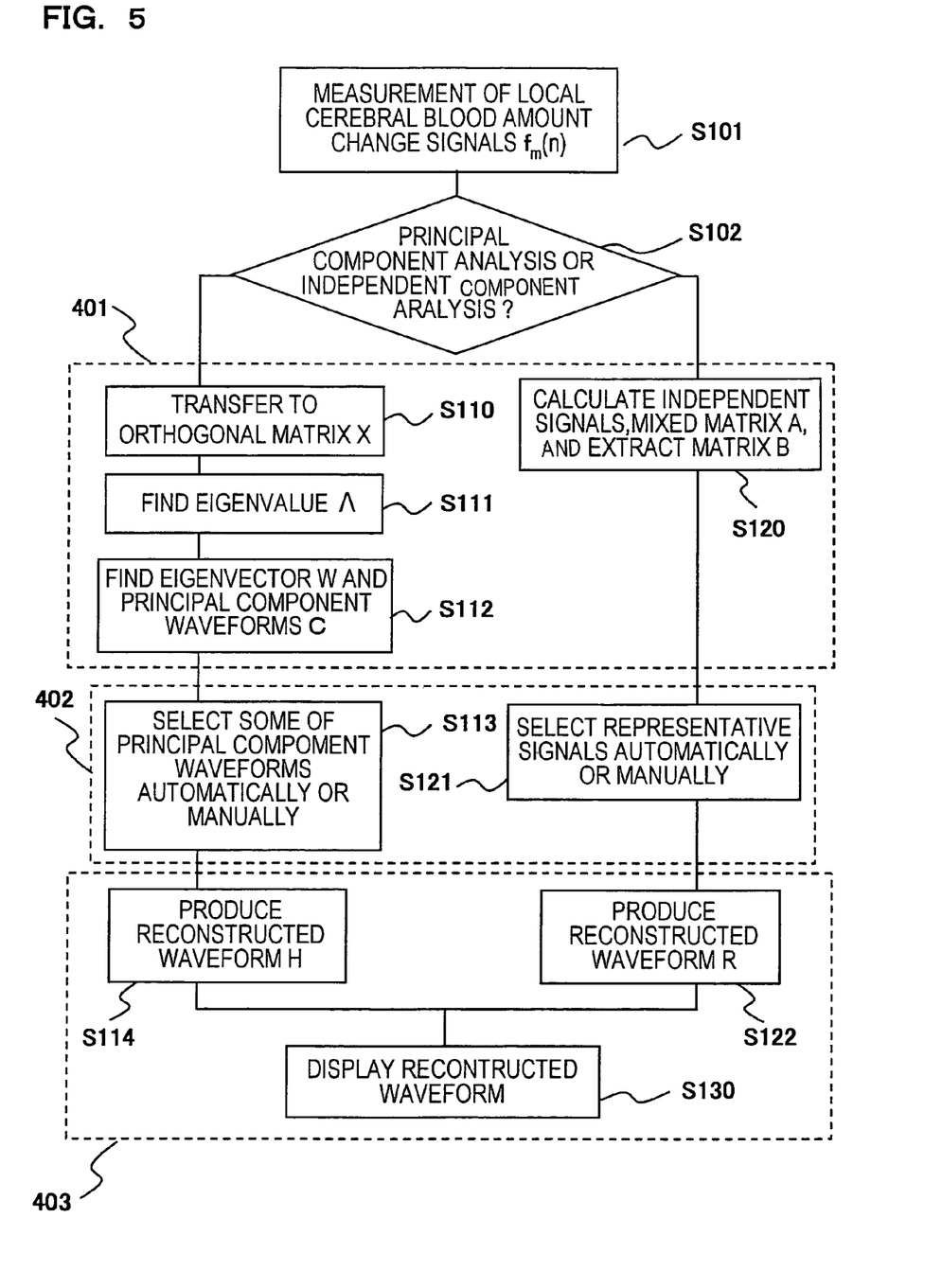
FIG. 5 is a flowchart showing the procedures for separating noise in the optical measurement apparatus for living body of this invention.

The noise separation to be performed at the signal processing unit 30 is explained below. FIGS. 4 and 5 show an embodiment of the signal processing procedure at the signal processing unit 30 and at the noise separation procedures, respectively.

The noise separation comprises mainly a processing 401, which separates the hemoglobin amount change signals into components and display them, a processing 402, which removes specified components of displayed components as noise components or select specified components for the use in the reconstruction, and a processing 403, which reconstructs the hemoglobin amount change signals by using the noise-removed components or the components selected for the use in the reconstruction. The optical measurement apparatus for living body displays the hemoglobin amount change signals as the time course waveforms as shown in FIG. 3, analyzes these waveforms, as required, identifies the sites most reactive to the task loaded and assesses cerebral diseases and others based on the characteristics of the response waveforms of the subject (processing 406).

In the embodiments of this invention, a step 401, which separates the hemoglobin amount change signals into components, adopts a principal component analysis or independent component analysis, and conduct the separation by selecting either of them or combining them.

The principal component analysis is a method to extract statistically uncorrelated signals by maximizing the variance without taking into account the components composing the measured hemoglobin amount change signals and the transfer function used to produce the measurement results. The independent component analysis, on the other hand, is a method to extract signals regarded as independent in terms of probability density by finding a transfer function in the assumption that the hemoglobin amount change signals are resulted from the linear combination of change signals from various cerebral sites and external signals in a correlated manner. The selection of either of these two analyses, or the combination of these two according to the characteristics of the noise ensures highly precise analysis. For example, when several signal sources are typical stereotyped noise, the independent component analysis is effective.

These principal component and independent component analyses are the component analysis technique whose algorithm has been established in the multi-variance analysis, and in the optical measurement apparatus of this embodiment a software for implementing the algorithm is built in at the signal processing unit 30 to perform said analysis by selecting either of the two or combining the two, as appropriate, through a user interface (GUI) at the input/output unit 33.

As shown in FIG. 3, the monitor at the input/output unit 33 displays the hemoglobin signals, which are measured at the optical measurement unit 20 and expressed by channel as the blood level of hemoglobin, along with a button 302 (CalcPCA) to select the principal component analysis and a button 303 (CalcICA) to select the independent component analysis. When either of them is selected on this screen 300, either of the principal component analysis (S11-S114) or independent component analysis (S120-S122) is implemented according to the procedures shown in FIG. 5 (S102).

When the principal component analysis is selected, orthogonal matrix $X_m(m)$ is produced from the local cerebral blood amount change signals $f_m(n)$ which are measured at the step S101 (S110).

Namely, the matrix F (where m is the line number, while n is the row number), which is the assembly of local cerebral blood amount change signals $f_m(n)$ (where, m is the channel number, and if M is the maximum measurable number of channels, $1 \leq m \leq M$. n is the time course data number corresponding to the abscissa of the graph 301, and if N is the maximum measurable time, $1 \leq n \leq N$) is produced, and then the orthogonal matrix X(M×M matrix) is produced from the matrix F and its transposed matrix $F^T$ by the following equation (1).

$$X = F \cdot F^T \quad (1)$$

When the transposed matrix $F^T$ of the matrix F is subjected to convolution from the right, the correlation average in the direction towards the time course data of optical measurement is obtained, whereas when it is subjected to convolution from the left, the correlation average in the direction towards the measurement channel of optical measurement is obtained. In this embodiment, the characteristics of time information of each space (channel) (characteristics in the direction of time course data) are extracted by the convolution from the right.

Then, matrix Λ of eigenvalues $\lambda_k$ (Step S111) is obtained for the afore-mentioned orthogonal matrix X, from which eigenvector W and the principal component waveform are calculated (Step S112). The eigenvalue is "the number of times of multiplications" of the eigenvector, and if a vector W becomes Λ folds when multiplied by matrix X, Λ is an eigenvalue and W is an eigenvector, and they are given by the following equations (2) and (3):

$$XW = \Lambda W \quad (2)$$

$$\Lambda = W^{-1} X W \quad (3)$$

M-dimensional matrix contains M eigenvalues and eigenvectors. By assuming that the matrix, in which M eigenvalues $\lambda_k$ ($1 \leq k \leq M$) to be calculated are arranged diagonally in the descending order (eigenvalue matrix) and solving the following equation (4) by substituting eigenvalue $\Lambda = \lambda_1$, eigenvalue $\Lambda = \lambda_2$ ... eigenvalue $\Lambda = \lambda_M$ for Λ of the equation (2), an eigenvector W is given.

$$(X - \Lambda) W = 0 \quad (4)$$

The eigenvector W is an M×M matrix consisting of M eigenvetors $w_k(m)$ ($w_1(1) \sim w_M(M)$, $1 \leq k \leq M, 1 \leq m \leq M$), and the k-th principal component waveform $Y_k$ of matrix X is given by the following equation (5).

$$Y_k = w_k^T X \quad (5)$$

Here, by using an original signal F instead of X, a principal component waveform $C_k$ of signal F ("k" indicates the k-th component, with $1 \leq k \leq M$) is obtained. This gives from 1-th to M-th principal component waveforms for the signal assemblies F.

$$C_k = W_k^T F \quad (6)$$

Figure 6:
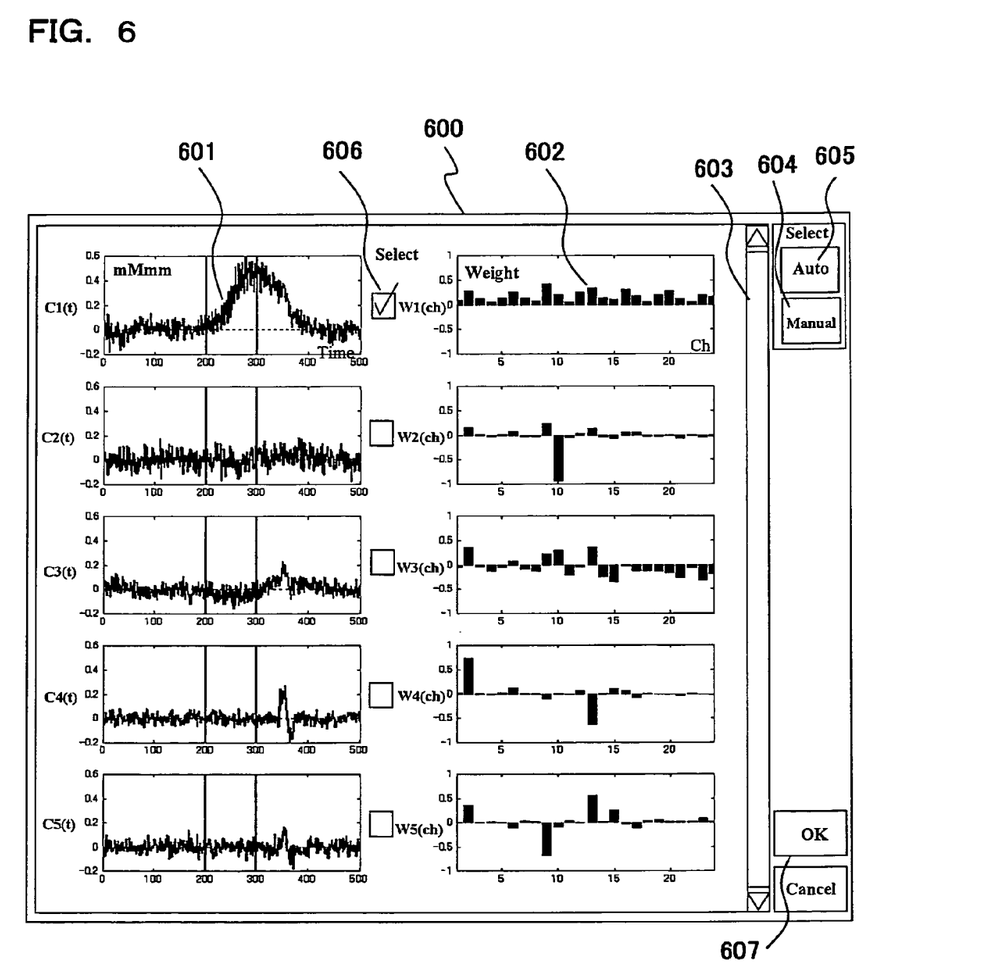
FIG. 6 is a diagram showing an example of a screen displaying principal component waveforms separated by the principal component analysis and eigenvectors.

The thus calculated principal component waveforms $C_1$-$C_k$ are displayed along with the eigenvector $W_k(m)$ on the monitor of the input/output unit 33. FIG. 6 is an example of the display (GUI). As shown in the figure, the first principal component waveform 601 $C_1(t)$, the second principal component waveform 602 $C_2(t)$ ... are displayed from the top in the left side of the screen, while the eigenvectors 602 $w_1(m)$, $w_2(m)$ ... are displayed on the right side of the screen. The eigenvectors show the weight (existence frequency) of the corresponding principal component waveform in each channel. The figure shows from first to 5th component waveforms. However, all of the calculated principal component waveforms can be seen by scrolling a slider bar 603.

The signals are reconstructed by removing noise waveforms from thus separated principal component waveforms (S113, FIG. 4: Processings 402 and 403). In this embodiment, either automatic or manual processing can be selected for the reconstruction of signals.

When a button 604 (Manual) for selecting manual processing is operated on the screen 600 which displays principal component waveforms and eigenvectors, as shown in FIG. 6, users will be able to check (input into) a selection box for selecting principal component waveforms. Users may select any waveform for the use in the reconstruction of signals by checking the selection box 606. When selecting component waveforms, the waveforms empirically considered noise are removed and those considered the main part of the signal components are used for reconstructing signals. For the component waveforms which can be classified in neither of them, a trial and error method is used to confirm the resulting waveforms by inputting or removing the non-classifiable component waveforms, during which reference can be made to the display of eigenvectors.

Figure 7:
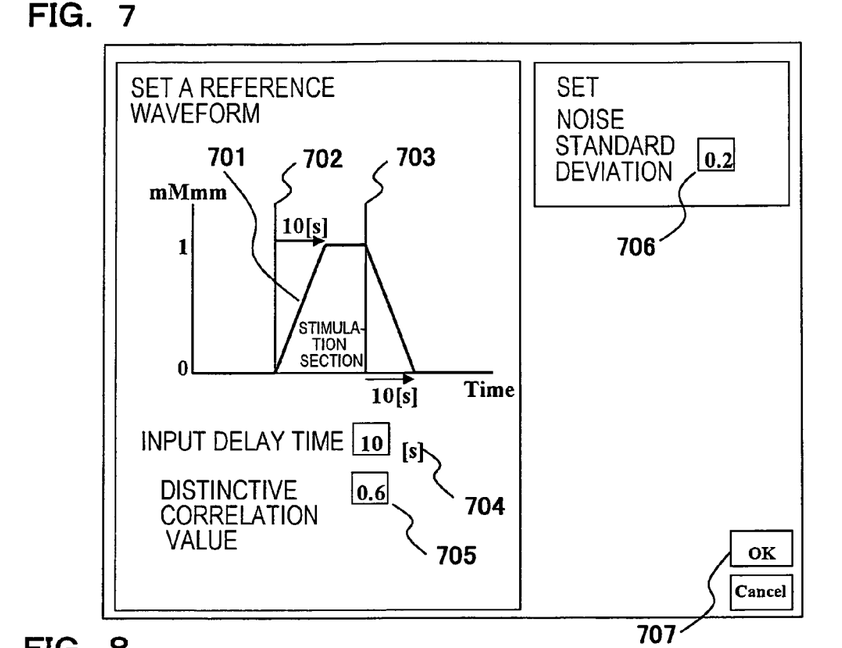
FIG. 7 is a diagram showing an example of GUI when the component waveform is selected automatically.

When a button 605 (Auto) for selecting automatic processing is operated, a screen for setting criteria for selecting component waveforms to be used in the reconstruction of waveforms is displayed. An example of the screen for setting selection criteria is shown in FIG. 7. In the illustrated example, either or both of two methods, (1) selecting the waveforms highly correlated with a reference waveform 701 and (2) selecting the waveforms with small standard deviations of differential waveform is used selectively or in combination.

As the reference waveform 701, the waveform empirically known as a signal (task-related signals or representative signals) that represents the characteristics of living body reactions to the task loaded during the measurement to the subject during measurement is used. In the illustrated embodiment of this invention, a basic trapezoidal reference waveform 701 is displayed, which users can transform appropriately according to the measurement conditions then or measured waveforms. For example, by inputting figures in a delay time input box 704, a trapezoid which can emerge at the inputted time is formed. Further, by moving two vertical lines 702 and 703, which represent the length of time while task is loaded (section of stimulation), the interval between stimulating sections and the stable section before and after the stimulating section can be set up. By inputting a correlation value in the distinctive correlation value box 705 after thus producing the reference waveform 701, and operating an OK button 707, the component waveform whose correlation value with this reference waveform is higher than the inputted correlation value can be selected.

Standard deviations of differential waveforms are calculated for the stable section before and after the stimulation section. The stable section is originally a section where the changes (differentials) in the hemoglobin change signals are small, so that differential waveforms with large standard deviations in this stable section are considered as noise components. Concretely, only the component waveforms with smaller standard deviations than the figures set in the standard deviation box 706 are selected for the use in reconstructing signals. Either or both of the afore-mentioned two methods can be used.

When the component waveform is selected automatically or manually, the signal processing unit 30 reconstructs signals (reconstruction) by using these selected waveforms (S114, FIG. 4: 403). For example, if the waveforms from the first component waveform C1 to the k-th component waveform $C_k$ are selected, signal $H_m$ (m is a channel number, $1 \leq m \leq M$) in each channel is reconstructed with eigenvalue wi corresponding to each component waveform by the following equation (7).

[Equation 1]

$$Hm = \sum_{i=1}^{k} wi(m) x Ci \qquad (7)$$

Figure 8:
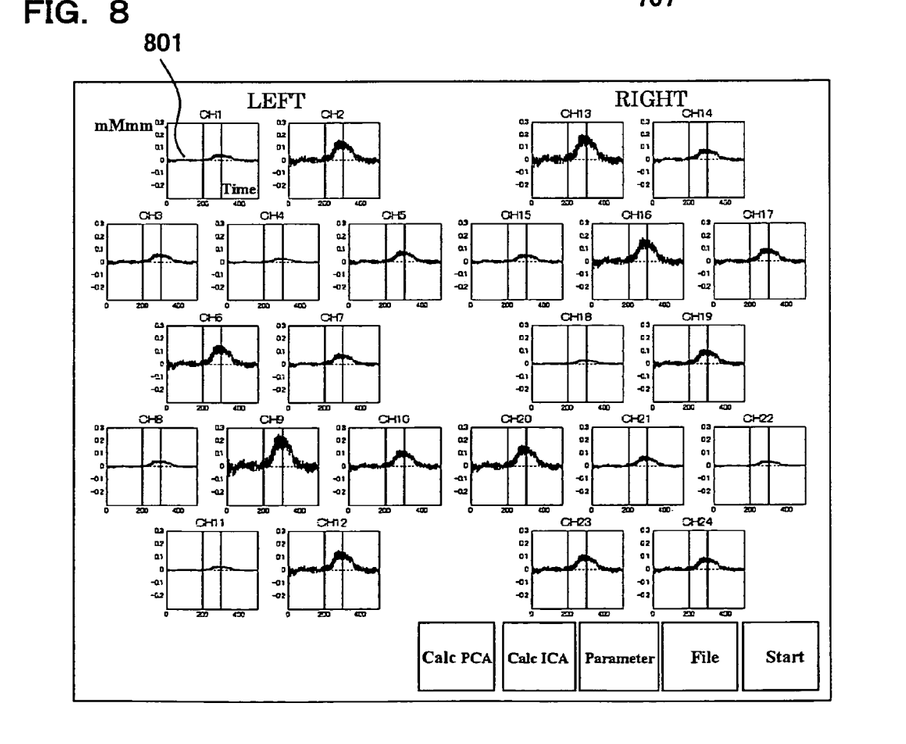
FIG. 8 is a diagram showing hemoglobin amount change signals after reconstruction.

Reconstructed signals are displayed on the monitor of the input/output unit 33 (FIG. 5: S130). An example of display is shown in FIG. 8. In this example, the screen displaying reconstructed signals 801 are made like the one for original signals (FIG. 3). Users can repeat the afore-mentioned processings 401-403, if it is deemed necessary in view of the reconstructed signals (FIG. 4: 405). In this case, principal component analysis (S110 0 S114) or independent component analysis (S120-S122) is implemented by using reconstructed signals. Further, as above mentioned, when the component waveform is selected manually, users can return to the component waveform selection step 402 in view of the reconstructed signals displayed on the screen and repeat a trial and error method (404).

The noise separation 402 by means of the independent component analysis is explained below. When a button (CalcICA) 303 to select the independent component analysis is operated on the screen 300 on which hemoglobin change signals are displayed (FIG. 3), the steps S120-S122 in FIG. 5 are implemented.

In the independent component analysis, it is assumed that this signal F (matrix of $f_m(n)$) is mixed by the signals of multiple (M') signal source vectors S(n) as given by the equation (8), and the independent signals, which is components of the signal F, the mixed matrix A of the independent signals and the extract matrix B for restoring component signals are calculated (S120).

$$F(n)=AS(n) \qquad (8)$$

(where, n is the time course data number, S(n) is a vector expressed with $S(n)=(S_1(n), S_2(n) \ldots S_{M'}(n))$ and the component $s_{m'}(n)$ ($1 \leq m' \leq M'$) are assumed to be mutually independent. A is a mixed matrix (transform matrix)).

The independent component analysis is a problem to find Y(n) which is defined by the following equation (9) by using only the measured signals F(n), but without any transcendental information on the probability distribution of S(n) and the mixed matrix A. If $M \geq M'$, a solution exists and the extract matrix B (a real number matrix of M×M') exists.

$$Y(n)=BX(n) \qquad (9)$$

In the embodiment of this invention, by taking account of case where M=M', and on the assumption that every component of S(n) is independent, an iterative method is used to find B which satisfies B×A=I(I is a unit matrix) and then Y(n) by the equation (9).

Figure 9:
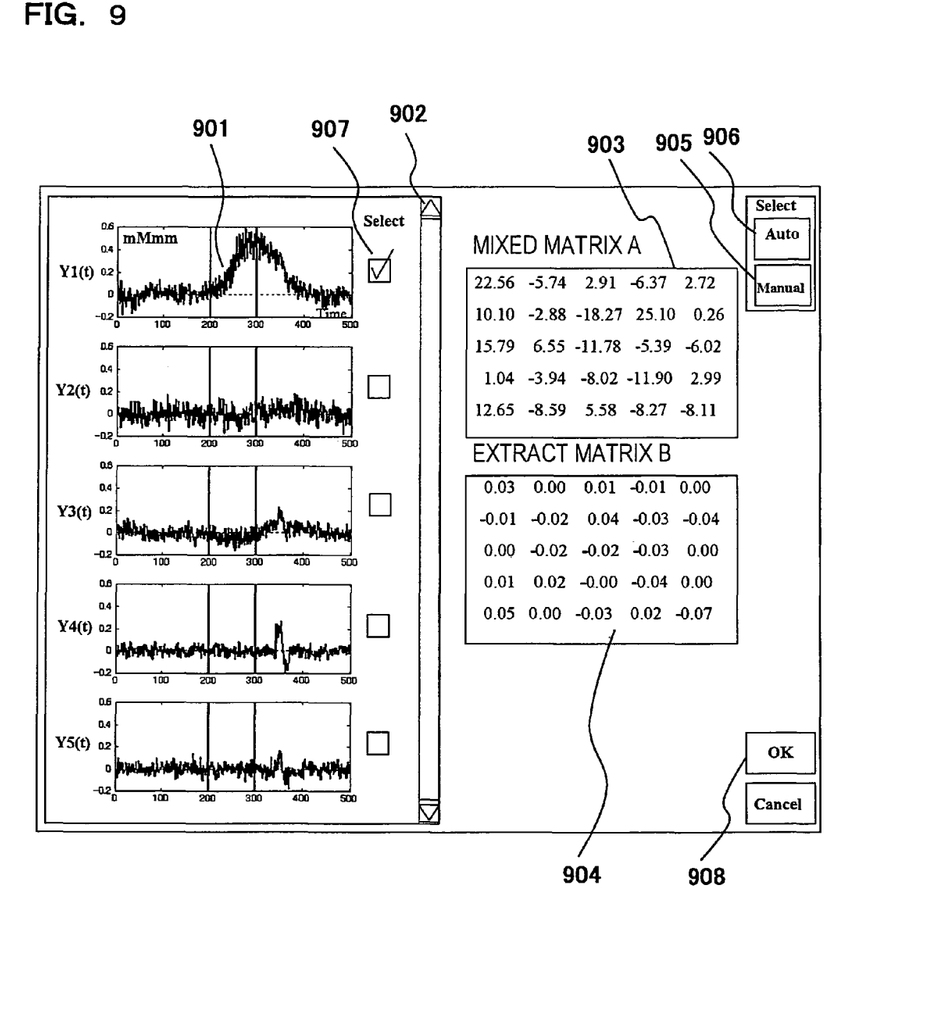
FIG. 9 is a diagram showing an example of a screen displaying component waveforms (independent signals) separated by the independent component analysis and a mixed matrix/extract matrix.

The independent component waveforms $Y_1$-$Y_M$ thus calculated are displayed on the monitor of the input/output unit 33, along with the mixed matrix A and the extract matrix B. FIG. 9 shows an example of the display (GUI). As illustrated, the first independent component waveform 901 $Y_1(t)$, the second independent component waveform $Y_2(t)$ . . . are displayed from the top in the left side of the screen, while the mixed matrix A 903 which corresponds to the weight (existence frequency) in mixing each component waveform and the extract matrix B 904, which corresponds to the weight in the extraction, are displayed on the right side of the screen. The figure illustrates the mixed matrix A and extract matrix B having shortened sizes than the actual size. In this case, all calculated independent component waveforms can be seen also by scrolling a slider bar 902.

Then, specified waveforms excluding noise waveforms are selected from thus separated independent component waveforms and used for reconstructing signals. Also in this case, like the signal separation by the principal component analysis, it can be chosen whether the signals are reconstructed automatically or manually (S121). When a button 905 (Manual) for selecting manual reconstruction is operated on the screen, which displays the independent component waveforms, as shown in FIG. 9, it becomes possible to check a selection button 907 (select) for selecting independent component waveforms. Users, therefore, can select any waveform for reconstructing signals by checking the selective button 907. These selection criteria are the same with those applied to the selection of the principal component waveforms, and users may repeat a trial and error method as required.

When a selection button 906 (Auto) for selecting automatic processing is operated, a screen (FIG. 7) for setting criteria for selecting component waveforms to be used in reconstructing waveforms is displayed, as in the case of principal component analysis. By setting reference waveforms and inputting necessary parameters according to the display on the screen, the selection of automatic component waveforms by the signal processing unit 30 is implemented.

When the component waveforms are thus selected either automatically or manually, the signal processing unit 30 reconstructs signals with selected waveforms (S122). For example, when the waveforms from the first component waveform $Y_1$ to the k-th component waveform $Y_k$ are selected, signals $R_m$, (m is the channel number, $1 \leq m \leq M$) are reconstructed with the values of the extract matrix Bi corresponding to each component waveform by the following equation (10).

[Equation 2]

$$R_m = \sum_{i=1}^{k} Bi(m) \times Yi \qquad (10)$$

The reconstructed signals are displayed on the monitor of the input/output unit 33. Users can repeat the afore-mentioned processings 401-403, if necessary, in view of the reconstructed signals displayed on said monitor (405). When the representative signals are selected manually, the processings 402 and 403 can be repeated as necessary (404).

As mentioned previously, the primary component analysis is a method to extract statistically uncorrelated signals, while the independent component analysis is a method for extracting signals which are independent in terms of probability density. A method capable of separating noise more easily depends on the characteristics of the noise. In this invention, either the principal component analysis or independent component analysis may be selected depending on the characteristics of noise, for example, and be implemented once or repeatedly for several times, or, both of them can be used in combination to ensure effective removal of various types of noises and to obtain more precise target signals.

The noise-removed signals are not only displayed as a time-course waveform as shown in FIG. 8 but also further processed to produce clinically useful information (Processing 406). For example, the most reactive site can be identified from the correlation with task-associated signals (identification of the linguistic area), or a disease can be diagnosed from the correlation with the stored task-associated signals of the patients with various cerebral diseases.

As an embodiment of this invention, the noise separation with the primary and independent component analyses has been explained above. This invention is not limited to the afore-mentioned embodiments, and it is also possible to use this invention along with the public known noise separation technology (filtering and moving averaging), as it is deemed necessary. Further, the GUI for selecting the noise separation procedure and the component waveforms is not limited to the one illustrated in this invention but can be modified appropriately. For example, the component analysis method can be selected from the menu displayed on the screen, rather than by the button operation. Or when the component analysis procedure is repeated for multiple times, the method of analysis and its order can be input.

INDUSTRIAL APPLICABILITY

According to this invention, the noise separation procedure by the component analysis of measured signals including hemoglobin amount change signals measured in the optical measurement can effectively remove noises regardless of the characteristics of the noise and obtain high-precision target signals. Further, according to the optical measurement apparatus of this invention, because the progress of signal processing can be monitored by means of user's interface and the conditions of signal processing can be set depending on the subject's individual difference and measurement conditions, the signals which are most similar to the original signals can be reproduced flexibly.

The invention claimed is:

1. An optical measurement apparatus for living body comprising a means for irradiating visible to infrared light onto an object to be examined, a means for detecting light transmitted inside said object and generates signals corresponding to the detected amount of light, a signal processing means for processing the signals and generating biological signals of the object to be examined and a display means for displaying the biological signals generated by said signal processing means; wherein said signal processing means comprises at least one signal separating means for separating the biological signals into multiple component signals, a signal selecting means for selecting specified component signals based on correlation values between component signals and a pre-determined reference waveform signal that represents a characteristic of living-body reaction of the examined object, and a signal reconstruction means for reconstructing the biological signals by using the selected specified component signals, excluding those containing noise, of said multiple component signals.

2. The optical measurement apparatus for living body according to claim 1, wherein said displaying means displays separated component signals and reconstructed signals, respectively.

3. The optical measurement apparatus for living body according to claim 1, wherein said signal processing means comprises at least two different signal separating means.

4. The optical measurement apparatus for living body according to claim 1, wherein at least one of said at least one signal separating means analyzes the principal components of said biological signals and separates them into multiple component signals.

5. The optical measurement apparatus for living body according to claim 1, wherein at least one of said at least one signal separating means analyzes the independent components of said biological signals and separates them into multiple component signals.

6. The optical measurement apparatus for living body according to claim 1, wherein said signal selecting means further selects the specified component signals based on the standard deviations of differential waveforms of the component signals.

7. The optical measurement apparatus for living body according to claim 1, wherein signal processing means comprises a user interface means with which users can select the selected specified component signals to be used by said signal reconstructing means.

8. The optical measurement apparatus for living body according to claim 1, wherein multiple principal component waveforms or independent component waveforms and a selecting box for selecting the multiple principal component waveforms or independent component waveforms are displayed.

9. The optical measurement apparatus for living body according to claim 1, wherein a correlation value box for inputting the correlation value and/or a standard deviation box for inputting the standard deviation are displayed in said display means.

10. An optical measurement apparatus for living body comprising a means for irradiating visible to infrared light onto multiple positions of an object to be examined, a means for detecting a light irradiated from said multiple positions and transmitted inside the object and generating measurement signals at multiple measurement points which are defined by the irradiating and detecting positions, a signal processing means for processing measurement signals detected by said detection means and generating waveforms indicating changes of substance inside the object at the multiple measurement points and a display means for displaying the results of processing by said signal processing means;
wherein said signal processing means comprises a signal separating means for separating the waveforms into multiple component waveforms, a signal selecting means for selecting specified component signals based on correlation values between component signals and a pre-determined reference waveform signal that represents a characteristic of living-body reaction of the examined object, and a signal reconstruction means for reconstructing waveforms representing changes in substance inside said object to be examined by using the selected specified component waveform among the multiple component waveforms.

11. A method of removing noise from the optical measurement signals of living body obtained by irradiating a light onto the examination site of an object to be examined and detecting a light transmitted through said examination site, comprises
a step of analyzing components of the optical measurement signals and separating them into multiple component signals, a step of selecting specified component signals based on correlation values between component signals and a pre-determined reference waveform signal, wherein the pre-determined reference waveform signal represents a characteristic of living-body reaction of the examined object, and a step of reconstructing optical measurement signals by using specified component signals among the separated multiple component signals.

12. The method of removing noise according to claim 11, wherein the step of separating measured signals into the multiple component signals comprises a step of performing a principal component analysis of the multiple component signals.

13. The method of removing noise according to claim 11 or 12, wherein the step of separating measured signals into the multiple component signals comprises a step of performing an independent component analysis of the multiple component signals.

14. The method of removing noise according to claim 11 or 12, which comprises a step for separating the optical measurement signals reconstructed by said reconstruction step into the multiple component signals and a step for reconstructing signals.

15. The method of removing noise according to claim 11 or 12, which comprises a step for selecting specified component signals from multiple separated component signals.

16. The method of removing noise according to claim 15, wherein the specified component signals are further selected by using correlation values between the component signals and a pre-determined reference signal and/or standard deviations of differential waveforms of the component signals in said selecting step.

\* \* \* \* \*